United States Patent [19]
Horn et al.

[11] 3,931,215
[45] Jan. 6, 1976

[54] BENZOFURAN DERIVATIVES

[75] Inventors: Anton Horn, Kelkheim, Taunus;
Erich Schinzel, Hofheim, Taunus;
Wilfried Sahm, Kelkheim, Taunus;
Günter Rösch, Altenhain, Taunus,
all of Germany

[73] Assignee: Hoechst Aktiengesellschaft,
Frankfurt, Germany

[22] Filed: Jan. 21, 1974

[21] Appl. No.: 435,276

[30] Foreign Application Priority Data
Jan. 26, 1973  Switzerland.......................... 1172/73

[52] U.S. Cl.................. 260/309.2; 8/1 W; 8/54.2;
8/162 R; 8/177 R; 8/179; 8/180; 260/240 R;
260/240 D; 260/240 E; 260/346.2 R;
260/346.2 M; 260/576; 260/577; 260/570.9;
260/578; 252/301.2 W; 252/301.3 W
[51] Int. Cl.²........................................ C07D 235/18
[58] Field of Search.................................. 260/309.2

[56] References Cited
UNITED STATES PATENTS

| 3,586,673 | 6/1971 | Bloom et al. | 260/309.2 |
| 3,766,199 | 10/1973 | Dehnert et al. | 260/309.2 |

OTHER PUBLICATIONS
C.A. 77: 128,095s (1972) Schlaepfer.

*Primary Examiner*—Sherman D. Winters
*Attorney, Agent, or Firm*—Connolly and Hutz

[57] ABSTRACT

Novel benzofuran containing a benzimidazolyl group are obtained by reacting a benzofuran containing a carboxylic acid halide group with either an ortho-phenylene diamine or an ortho-nitro-aniline derivative, in the latter case reducing the nitro intermediate to the corresponding (aminophenyl)-amide and splitting off water by closing the imidazole ring. The products are optical brighteners, especially for acrylonitrile polymers.

10 Claims, No Drawings

BENZOFURAN DERIVATIVES

The present invention relates to benzofuran derivatives to a process for their preparation and their use as optical brighteners.

It is already known how to prepare benzofuran derivatives in which an optionally quarternized benzimidazolyl radical is placed in 2-position. It is furthermore known to use these compounds as optical brighteners for organic materials (German Offenlegungsschriften Nos. 2,031,774 and 2,159,469).

The present invention relates to benzofuran derivatives of the general formula (I)

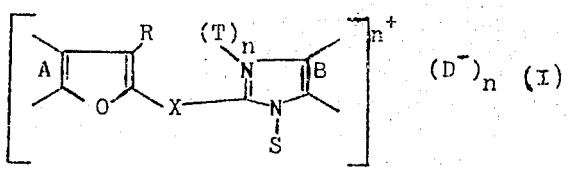

In this formula A and B represent two aromatic mono- or polynuclear ring systems, which may be identical or different wherein two adjacent carbon atoms are condensed with the furan or imidazol nucleus, R is hydrogen, a lower alkyl group, a phenyl group which may be substituted by lower alkyl or alkoxy groups or halogen atoms or an optionally modified carboxy group, X represents a continuously conjugated chain of carbon atoms, which may be completely or partly a constituent of a carbocyclic or heterocyclic ring system and is conjugated with the adjacent furan and imidazole ring, S represents a hydrogen atom, a lower alkyl or cyanoethyl group, an aralkyl group, preferably a lower alkyl group substituted by a phenyl group; or a phenyl group which may be substituted by halogen atoms, lower alkyl or alkoxy groups; T is a lower alkyl group, an optionally substituted aralkyl group, preferably a lower alkyl group substituted by a phenyl group; or a group of the formula
—CH₂—CN, —CH₂—CO—NH₂, —CH₂—COOE,
E representing a hydrogen atom or a lower alkyl groups; D⁻ is a colorless anion and $n$ being zero or 1.

Non-chromophoric substituents may be bound to the aromatic ring systems A and B and to the middle component X.

The term "lower", when used in connection with aliphatic radicals is intended to cover groups of up to 4 carbon atoms. As non-chromophoric substituents there may be considered halogen atoms, (preferably lower) alkyl, (preferably lower) alkylene, (preferably lower) alkoxy, (preferably lower) alkenyl, aryl, especially phenyl groups, carboxy or sulfo groups optionally having modified functions, acyl, acylamino or sulfonyl groups. There may also be bound several of the mentioned groups which may be identical or different from one another, simultaneously to A, B and X.

A carboxy group having modified functions means first the salts of this group formed with colorless cations, alkali metal or ammonium ions being preferred, and furthermore the functional derivatives of a carboxy group, from the carbon atom of which three bonds lead to hetero atoms, especially as in the cyano group, a carboxylic ester group or carboxylic acid amide group.

Carboxylic acid ester groups are especially those having the general formula COOR¹, in which R¹ represents a phenyl radical or an optionally branched lower alkyl radical, wherein these radicals may contain further substituents, for example, a hydroxy, a preferably low-molecular dialkylamino, trialkylammonium or alkoxy group. A carboxylic acid amide group is especially a group having the formula CONR²R³, in which the radicals R² and R³ represent hydrogen atoms or lower alkyl groups which may be substituted, especially by hydroxy groups, which alkyl groups may form with the nitrogen atom a hydroaromatic ring, such as a piperidino or morpholino ring, furthermore the hydrazides and the analogous thioamides.

A sulfo group having modified functions, by analogy to the preceding explanations, represents the salts of this group formed with colorless cations, preferably alkali metal or ammonium ions and furthermore the derivatives, in which the SO₂ group is bound to a hetero atom, as in the sulfonic acid ester group and in the sulfonamide group. The sulfonic acid ester group especially means a group of the formula SO₂OR¹, wherein R¹ has the above meaning, and a sulfonic acid amide group means a group of the formula SO₂NR²R³, in which R² and R₃ have the above-mentioned meaning.

An acyl group is especially a group of the formula COR⁴, wherein R⁴ represents an optionally substituted, preferably lower alkyl or a phenyl radical.

A sulfonyl radical is especially a radical having the formula SO₂R⁵, wherein R⁵ represents an optionally substituted lower alkyl or a phenyl group; these groups may preferably contain, as substituents, a lower dialkylamino, trialkyl ammonium, acylamino or sulfo groups.

Among the compounds of the general formula (I) there are especially interesting those having the general formula (II)

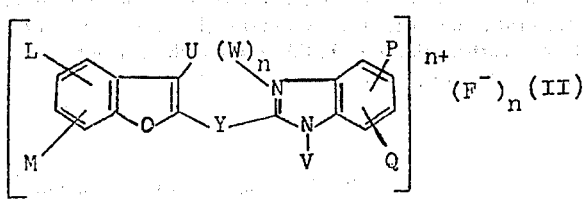

In this formula
L and M, which may be identical or different, as well as P and Q which also may be identical or different, represent hydrogen or halogen atoms, lower alkyl or alkoxy groups, phenyl groups, or together an annellated benzene nucleus, U is a hydrogen atom, a lower alkyl or phenyl group, V is a hydrogen atom, a lower alkyl group, a benzyl group, or a phenyl group which is optionally substituted by chlorine atoms, methyl or methoxy groups; W is a lower alkyl group, a benzyl group which is optionally substituted by chlorine atoms, methyl or methoxy groups; or a radical of the formula
—CH₂—CN, —CH₂—CO—NH₂, —CH₂—COOG,
wherein G represents a lower alkyl group; Y is a group of the formula

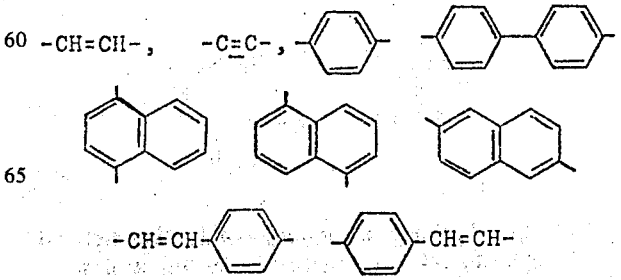

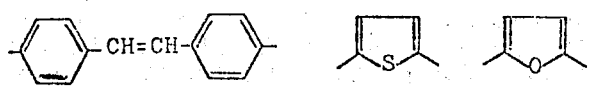

preferably ethenylene, phenylene, naphthylene or 1,4'-styrylene, n represents zero of 1, and F represents a halogen or lower alkylsulfate ion, a lower alkylsulfonic acid anion or an optionally methylsubstituted phenylsulfonic acid anion.

The compounds of the invention may be prepared according to the processes described in the following section, the radicals A, B, X, R and S having the meaning indicated in the general formula (I).

The preferred processes of preparation comprises reacting either a. the acid halide, especially the acid chloride of the general formula (III)

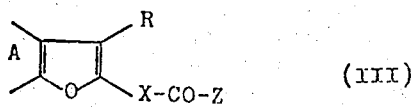

in which Z represents a halogen, especially a chlorine atom, with a salt of a p-phenylene-diamine of the general formula (IV)

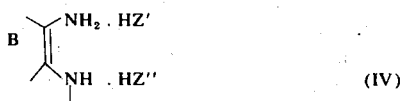

wherein S' has the same meaning as S, but not a hydrogen atom, and Z' and Z'' represent monovalent anions, preferably halogen and especially chlorine atoms, or b. converting the acid halide (III) with an o-nitro-aniline of the general formula (V)

into the o-nitro-acylamino compound of the general formula (VI)

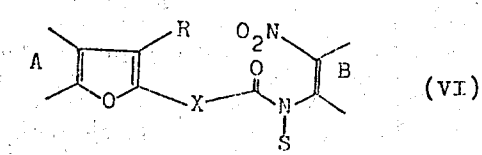

and furthermore reducing the compound (VI) either to the amine of the general formula (VII)

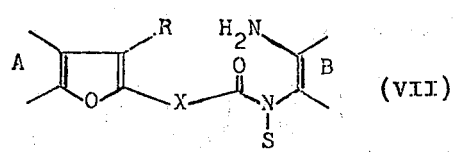

and converting this amine into the imidazol compound (I) by splitting off water, or by converting it in many cases directly into the imidazol compound (I) with the aid of a modified Béchamp reduction.

The quarternary compounds are obtained from the N'-unsubstituted imidazols (I; $n=0$) by reaction with a quarternization agent of the formula (VIII)

$$T - D,$$

wherein T and D have the meanings indicated.

Naturally, compounds of the formula (I), in which S stands for a hydrogen atom, may be converted first in known manner into compounds wherein S has the other meanings, and these compounds may subsequently be quarternized.

The reaction of the acid halide (III) with the o-phenylenediamine (IV) is preferably carried out in an inert organic solvent. Preferably, a solvent is used, the boiling point of which is above about 150°C, in order to be able to work without applying pressure.

Suitable solvents are for example: o-dichloro-benzene, 1,2,4-trichlorobenzene or technical trichlorobenzene mixtures, 1-chloronaphthalene, methyl benzoate and nitrobenzene.

The reaction temperature depends on the radicals A, B, X, R and S and ranges between about 150° and about 250°C, preferably between about 180° and about 220°C.

The o-nitro-acylamino compound (VI) is prepared by heating the acid halide (III) with the o-nitro-aniline (V) in a solvent inert towards the reactants, to a temperature of about 50° to about 200°C, preferably about 80° to about 150°C. As inert solvents may be used for example; benzene, toluene, chlorobenzene, o-dichlorobenzene or xylene.

The reduction of the nitro compound (VI) is effected according to known methods, preferably by catalytic hydrogenation. The reduction is preferably carried out in a stirring autoclave in the presence of Raney-Nickel at room temperature and while using an inert solvent. There may be mentioned for example: ethanol, dioxane, N,N-dimethylformamide and chlorobenzene.

The reduction of the compound (VI) according to Bechamp with iron powder in the presence of a small amount of acid is preferably carried out in a mixture of water and a well-water-soluble solvent. The mixture ratio ranges of from about 1 : 1 to about 1 : 10, preferably between about 1 : 5 and about 1 : 7. The reaction temperature depends on the boiling point of the solvent-water-mixture applied to each case and ranges between about 100° and about 200°C, preferably between about 120° and about 160°C. As solvents there may be used in this modified Bechamp reduction for example glycolmonomethyl ether or dimethylformamide. In many cases the ring-closed compound (I) is obtained directly, in some cases mixtures of the compounds (VII) and (I) are obtained.

The ring closure of the amine (VII) to the imidazol (I) is most successfully effected by heating to a temperature of about 150° to about 250°C, preferably about 180° to about 220°C in an inert solvent having a sufficiently high boiling point in the presence of an acidic catalyst. Examples for suitable solvents are: o-dichlorobenzene, 1,2,4-trichlorobenzene or nitrobenzene. As acidic catalysts may be used for example: zinc chloride, p-toluene-sulfonic acid or boric acid.

For the synthesis of the imidazoles (I) there may be used for example the acid chlorides of the following carboxylic acids:

β-[benzofuranyl-(2)]-acrylic acid,
β-[3-methyl-benzofuranyl-(2)]-acrylic acid,

β-[6-methyl-benzofuranyl-(2)]-acrylic acid,
β-[5,6-dimethyl-benzofuranyl-(2)]-acrylic acid,
β-[6-methoxy-benzofuranyl-(2)]-acrylic acid,
β-[6-tert.-butyl-benzofuranyl-(2)]-acrylic acid,
2-[p-carboxy-phenyl]-benzofuran,
2-[p-carboxy-phenyl]-3-methyl-benzofuran, 2-[p-carboxy-phenyl]-3-phenyl-benxofuran,
2-[p-carboxy-phenyl]-6-methyl-benzofuran,
2-[p-carboxy-phenyl]-6-methoxy-benzofuran,
2-[p-carboxy-phenyl]-6-tert.-butyl-benzofuran,
2-[p-carboxy-phenyl]-5,6-dimethyl-benzofuran,
2-[p-carboxy-phenyl]-naphtho-[1,2-d]-furan,
2-[p-carboxy-phenyl]-naphtho-[2,1-d]-furan,
2-[p-carboxy-phenyl]-naphtho-[2,3-d]-furan,
4-[benzofuranyl-(2)]-diphenyl-carboxylic acid-(4'),
4-[3-methyl-benzofuranyl-(2)]-diphenyl-carboxylic acid-(4'),
4-[6-methyl-benzofurnayl-(2)]-diphenyl-carboxylic acid-(4'),
4-[6-methoxy-benzofuranyl-(2)]-diphenyl-carboxylic acid-(4'),
4-[5,6-dimethyl-benzofuranyl-(2)]-diphenyl-carboxylic acid-(4'),
1-[benzofuranyl-(2)]-naphthalene-carboxylic acid-(4),
1-[3-methyl-benzofuranyl-(2)]-naphthalene-carboxylic acid-(4),
1-[6-methyl-benzofuranyl-(2)]-naphthalene-carboxylic acid-(4),
1-[5,6-dimethyl-benzofuranyl-(2)]-naphthalene-carboxylic acid-(4),
1-[benzofuranyl-(2)]-naphthalene-carboxylic acid-(5),
1-[3-methyl-benzofuranyl-(2)]-naphthalene-carboxylic acid-(5),
1-[6-methyl-benzofuranyl-(2)]-naphthalene-carboxylic acid-(5),
1-[6-methoxy-benezofuranyl-(2)]-naphthalene-carboxylic acid-(5),
1-[5,6-dimethyl-benzofuranyl-(2)]-naphthalene-carboxylic acid-(5),
2-[benzofuranyl-(2)]-naphthalene-carboxylic acid-(6),
2-[3-methyl-benzofuranyl-(2)]-naphthalene-carboxylic acid-(6),
2-[6-methyl-benzofuranyl-(2)]-naphthalene-carboxylic acid-(6),
2-[6-methoxy-benzufuranyl-(2)]-naphthalene-carboxylic acid-(6),
2-[5,6-dimethyl-benzofuranyl-(2)]-naphthalene-carboxylic acid-(6),
2-[p-carboxy-styryl]-benzofuran,
2-[p-carboxy-styryl]-3-methyl-benzofuran,
2-[p-carboxy-styryl]-6-methyl-benzofuran,
2-[p-carboxy-styryl]-6-methoxy-benzofuran,
2-[p-carboxy-styryl[-5,6-dimethyl-benzofuran,
p-[benzofuranyl-(2)]-cinnamic acid,
p-[3-methyl-benzofuranyl-(2)]-cinnamic acid,
p-[6-methyl-benzofuranyl-(2)]-cinnamic acid,
p-[6-methoxy-benzofuranyl-(2)]-cinnamic acid, 1-[6-methoxy-benzofuranyl-(2)]-naphthalene-carboxylic acid-(4),
p-[5,6-dimethyl-benzofuranyl-(2)]-cinnamic acid,
4-[benzofuranyl-(2)]-stilbene-carboxylic acid-(4'),
4-[3-methyl-benzofuranyl-(2)]-stilbene-carboxylic acid-(4'),
4-[6-methyl-benzofuranyl-(2)]-stilbene-carboxylic acid-(4'),
4-[6-methoxy-benzofuranyl-(2)]-stilbene-carboxylic acid-(4'),
4-[5,6-dimethyl-benzofuranyl-(2)]-stilbene-carboxylic acid-(4'),
2-[benzofuranyl-(2)]-thiophen-carboxylic acid-(5),
2-[3-methyl-benzofuranyl-(2)]-thiophene-carboxylic acid-(5),
2-[6-methyl-benzofuranyl-(2)]-thiophene-carboxylic acid-(5),
2-[6-methoxy-benzofuranyl-(2)]-thiophene-carboxylic acid-(5),
2-[5,6-dimethyl-benzofuranyl-(2)]-thiophene-carboxylic acid-(5),
2-[benzofuranyl-(2)]-furan-carboxylic acid-(5),
2-[3-methyl-benzofuranyl-(2)]-furan -carboxylic acid-(5),
2-[6-methyl-benzofuranyl-(2)]-furan -carboxylic acid-(5),
2-[6-methoxy-benzofuranyl-(2)]-furan -carboxylic acid-(5) or
2-[5,6-dimethyl-benzofuranyl-(2)]-furan -carboxylic acid-(5).

For preparing the imidazols (I) according to the variant of the process (a) there may be used for example the salts, preferably hydrohalides, especially hydrochlorides of the following N-substituted o-phenylene diamines:
o-amino-N-methylaminobenzene,
o-amino-N-ethylaminobenzene,
o-amino-N-n-butylaminobenzene,
o-amino-N-benzylaminobenzene,
o-amino-N-cyclohexylaminobenzene,
2-amino-4-methyl-N-methylaminobenzene,
2-amino-5-methyl-N-methylaminobenzene,
2-amino-4,5-dimethyl-N-methylaminobenzene,
2-amino-4-chloro-N-methylaminobenzene,
2-amino-5-chloro-N-methylaminobenzene,
2-amino-4-methyl-5-chloro-N-methylaminobenzene,
2-amino-4-chloro-5-methyl-N-methylaminobenzene,
2-amino-diphenylamine,
3-chloro-2-amino-diphenylamine,
4-chloro-2-amino-diphenylamine,
5-chloro-2-amino-diphenylamine,
3'-chloro-2-amino-diphenylamine,
4'-chloro-2-amino-diphenylamine,
4,4'-dichloro-2-amino-diphenylamine,
4,4'-dichloro-2-amino-diphenylamine,
4,5'-dichloro-2-amino-diphenylamine,
4-methyl-2-amino-diphenylamine or
5-chloro-3'-methyl-2-amino-diphenylamine.

For preparing the imidazoles (I) according to the variant of the process b), for example the following n-nitroanilines are suitable:
o-nitroaniline,
2-nitro-4-chloroaniline,
2-nitro-4-methylaniline,
2-nitro-4-methoxyaniline,
2-nitro-4-chloro-5-methylaniline,
2-nitro-4-methoxy-5-methylaniline,
2-nitro-4,5-dimethylaniline,
2-nitro-5,6-dimethylaniline,
2-nitro-5-methylaniline,
o-nitro-N-methylaminobenzene,
o-Nitro-N-ethylaminobenzene,
o-Nitro-N-n-butylaminobenzene,
o-nitro-N-cyclohexylaminobenzene,
o-nitro-N-benzylaminobenzene,
2-nitro-4-methyl-N-methylaminobenzene,
2-nitro-5-methyl-N-methylaminobenzene,
2-nitro-4,5-dimethyl-N-methylaminobenzene, 2-nitro-5,6-dimethyl-N-methylaminobenzene,
2-nitro-4-chloro-N-methylaminobenzene,
2-nitro-4-methoxy-N-methylaminobenzene or
2-nitro-4-chloro-5-methyl-N-methylaminobenzene.

The quarternization of the N-substituted imidazol compounds (I) is expediently carried out in an inert organic solvent while using a suitable quarternization agent. Suitable solvents are for example benzene, toluene, chlorobenzene, o-dichlorobenzene and 1,2,4-trichlorobenzene.

The reaction temerature of quaternization is in the range of from about 50° to about 200°C, preferably between about 80° and about 150°C.

Suitable quaternization agents are for example: methyl iodine, n-butyl bromide, benzyl chloride, dimethyl sulfate, diethylsulfate, benzene-sulfonic acid methyl ester or p-toluene-sulfonic acid methyl ester.

The carboxylic acids being the basis of the acid halides (III) are obtained according to known processes. Furthermore, a process has been proposed (German Offenlegungsschrift No. 2,238,628) according to which ether compounds of the general formula (VIIIa)

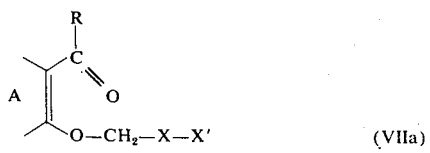

(VIIa)

in which A, R and X have the meaning indicated in formula (I) and X' is a carboxy group having modified functions, especially the cyano group, a carboxylic acid ester group, or a carboxylic acid amide group, are converted by intramolecular condensation into furan compounds of the general formula (IX)

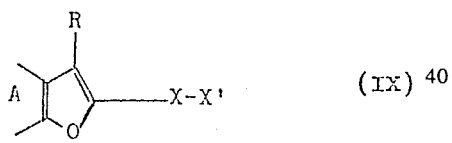

(IX)

These compounds may subsequently be saponified in an acidic or alkaline medium.

The intramolecular condensation of the ether compounds (VIIIa) to form the furan compounds (IX) is preferably carried out in the presence of strongly basic condensation agents. Examples for suitable solvents are dimethylformamide, dimethylacetamide and hexamethyl-phosphoric acid-trisamide. Mixtures of suitable solvents may also be used. As strongly alkaline condensation agents for the ring closure reaction there may be considered inter alia the alkali metals of alkaline earth metals and their strongly basic compounds as well as the corresponding aluminum compounds, as for example the hydroxides, alcoholates, amides or hydrides. Preferably, the corresponding sodium or potassium compounds are used, for example potassium hydroxide, potassium-tert.butylate or sodium hydroxide. A mixture of different bases may also be used. The alkaline condensation agents are usually used in the equivalent amount, partly in higher stoichiometrical amounts, for example in up to ten times the molar equivalent amount. The reaction temperature ranges between about 10° and 250°C, preferably between about 20° and 160°C. The reaction is preferably carried out with exclusion of air.

The products of the process of the formula (I) may be modified by further known reactions; for example, N-substituted imidazols may be alkylated, or carboxy or sulfo groups present may be converted into functionally modified derivatives or carboxy or sulfo groups having modified functions may be converted into the free acids or other derivatives. Furthermore, sulfo groups may be introduced subsequently by sulfonating the reaction products (I), for example with oleum, chlorosulfonic or amidosulfonic acid.

The novel compounds according to the invention show a more or less marked fluorescent power. The maximum of the fluorescence bands generally ranges between 400 and 460 nm, thus these compounds are very suitable for the optical brightening of natural and synthetic organic materials.

The substrates to be brightened are for example: natural fibres, such as cotton, synthetic fibres, for example fibres of acetyl cellulose, linear polyesters, polyolefins, polyvinyl chloride, polyvinylidene chloride, polystyrene and especially polyacrylonitrile, as well as films foils, ribbons or shaped articles of such synthetic materials. The synthetic material may be brightened for example by incorporating into it the optical brightener of the formula (I), if desired, together with other substances such as plasticizers, stabilizers or pigments.

Thus, the brightener may be incorporated into the plastic masses. Furthermore, it is possible to dissolve the brightener before the preparation of the plastic material in the monomeric starting materials before polymerization or polycondensation, or in the polymer mass, or together with the polymers in a solvent before shaping. The material thus pre-treated is then brought into the final form desired according to known processes such as polymerization, condensation, casting, spinning or stretching.

Preferably high-molecular organic material in the form of fibres is brightened. To brighten these fibre materials an aqueous solution of dispersion of the benzofuran of the invention having the general formula (I) is preferably used.

As far as the compounds of the invention are insoluble in water, they may also be dissolved in organic solvents or preferably used in a finely divided form by means of a dispersing agent.

Dispersing agents are for example soaps, polyglycol ethers deriving from fatty alcohols, fatty amines or alkyl phenols, cellulose sulfite waste liquors or condensation products of optionally alkylated naphthalene sulfonic acids with formaldehyde.

The fibre material is preferably brightened with an aqueous brightening liquor, either in the exhaustion process at temperatures of preferably 30° to 150°C or in the foulard process (padding process).

Especially good brightening effects are obtained with the benzofurans according to the invention of the formula (I) on fibre material from polyacrylonitrile in the presence of bleaching agents, for example sodium chloride.

High-molecular organic materials optically brightened according to the invention, especially natural or synthetic fibre material brightened according to the exhaustion process, show a clear white and brilliant appearance having a slightly greenish to reddish fluorescence.

Benzofurans of the general formula (I) may also be added to detergents. These detergents may contain the usual fillers and auxiliaries, for example, alkali silicates, alkali polyphosphates and alkali polymethaphosphates, alkali borates and alkali salts of the carboxymethyl cellulose, foam stabilizers, as for example, alkanol amides of higher fatty acids, or complex formers, for example soluble salts of the ethylenediamine-tetraacetic acid of diethylene-triamine-pentaacetic acid as well as chemical bleaching agents, such as perborates or percarbonates, perborate activators or disinfectants.

Such washing liquors containing benzofurans of the general formula (I) provide on textile fibres treated with them, for example synthetic polyamide, polyester and cellulose fibres, especially polyacrylonitrile fibres, a brilliant appearance in the day-light.

The amount of the compounds to be used according to the invention and corresponding to the general formula (I), calculated on the material to be optically brightened may vary within wide limits according to the field of application and the effect desired. It may be easily determined by tests and generally ranges between about 0.01 and about 2 %.

In the following Examples parts and percentages are by weight unless otherwise stated. The ratio of parts by weight to parts by volume is that of the kilogram to the litre.

The Examples A to D illustrate the process for preparing the compounds according to the invention.

EXAMPLE A:

Preparation of 2-[p-carboxy-phenyl]-benzofuran (Table 1, No. 101)

21.9 g of 2-[p-cyanophenyl]-benzofuran were introduced, while stirring, into 600 ml of glycol and after addition of 12 g of potassium hydroxide, heated, while stirring, for 15 minutes up to 165°-170°C. Then the mixture was cooled to 120°C and 235 ml of 2N-sulfuric acid were introduced dropwise.

The reaction mixture was poured into 1200 ml of water and stirred for 2 hours at room temperature. The product precipitated was suction-filtered, washed with water and dried. For purification the crude product was recrystallized from o-dichloro-benzene or 1,2,4-trichlorobenzene. 22.6 g (95 % of the theory) of 2-[p-carboxyphenly]-benzofuran (Table 1, No. 101) having a melting point of 301° to 302°C were obtained.

In analogous manner were prepared the other carboxylic acids listed in Table 1, by alkaline saponification of the corresponding nitriles or carboxylic acid ester.

TABLE 1:

| No. | R¹ | R² | R³ | R⁴ | X | melting point °C |
|---|---|---|---|---|---|---|
| 101 | H | H | H | H |  | 301 - 302 |
| 102 | H | H | H | —CH₃ |  | 219 - 220 |
| 103 | H | —CH₃ | —CH₃ | H |  | 350 - 352 |
| 104 | H | H | —O—CH₃ | H |  | 274 - 275 |
| 105 | H | H | H | H |  | 224 - 225 |
| 106 | H | H | H | H |  | 224 - 226 |
| 107 | H | H | H | H | —CH=CH—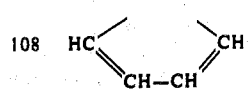 | 300 - 303 |
| 108 |  | | H | H | | 299 - 300 |

EXAMPLE B:

Preparation of
1-[benzofuranyl-(2)]-4-[1-methyl-benzimidazolyl-(2)]-benzene (Table 2, No. 201)

23.8 g of 2-[p-carboxy-phenyl]-benzofuran (101) were suspended in 150 ml of benzene. 25 ml of thionyl chloride were added and the reaction mixture was heated, while stirring, for 2 hours to 80°C. During this time the carboxylic acid was completely dissolved. Benzene and excess thionyl chloride were distilled off completely and the residue was taken up in 150 ml of o-dichlorobenzene. To this solution were then added 19.5 g of N-methyl-o-phenylene-diamine-dihydrochloride and heated, while stirring, in the course of one hour, to about 175°C. At about 140°C a vigorous development of hydrogen chloride began and at 160°C water was split off. The temperature was maintained for about 1 hour at 175°C, and the water formed in the reaction and a small amount of o-dichlorobenzene were distilled off over a descendant cooler. After cooling the reaction mixture to room temperature, 100 ml of concentrated aqueous ammonia solution were added, the mixture was stirred well and was subjected to steam distillation.

The distillation residue was suction-filtered, washed with water and dried.

For purification this crude product was recrystallized from n-butylalcohol while clarifying with charcoal. 23 g (71 % of the theory) of 1-[benzofuranyl-(2)]-4-[1-methyl-benzimidazolyl-(2)]-benzene (Table 2, No. 201) having a melting point of 192° to 193°C were obtained.

In analogous way were prepared the other imidazolyl compounds listed in Table 2.

TABLE 2

| No. | $A^1$ | $A^2$ | $A^3$ | $A^4$ | melting point °C | absorption $\lambda$max nm | $\epsilon \cdot 10^{-4}$ |
|---|---|---|---|---|---|---|---|
| 201 | H | H | H | H | 192–193 | 334 | 4,88 |
| 202 | H | H | H | $CH_3$ | 169–170 | 332 | 4,60 |
| 203 | H | $CH_3$ | $CH_3$ | H | 208–209 | 340 | 5,08 |
| 204 | HC=CH (fused) | | | H | 188–189 | 357 | 5,09 |

EXAMPLE C:

Preparation of
1-[3-methyl-benzofuranyl-(2)]-4-[benzimidazolyl-(2)]-benzene (Table 3, No. 302)

1. 4-[3-methyl-benzofuranyl-(2)]-benzoic acid-o-nitrophenylamide 25.2 g of 2-[p-carboxy-phenyl]-3-methyl-benzofuran (Table 1, No. 102) were suspended in 300 ml of benzene. 20.8 g of phosphorus pentachloride were added, and the whole was refluxed while stirring for two hours. Then it was filtered hot and the benzene and the $POCl_3$ formed were completely distilled off. The residue was taken up in 300 ml of chlorobenzene and mixed with 13.8 g of o-nitro-aniline. The reaction mixture was heated for 15 hours to the boil and the hydrogen chloride formed was removed by passing a moderate nitrogen stream through the reaction mixture.

Finally the reaction solution was clarified with charcoal and cooled to room temperature. The crystallized product was suction-filtered, washed with chlorobenzene and dried. 33.5 g (90 % of the theory) of 4-[3-methyl-benzofuranyl-(2)]-benzoic acid-o-nitro-phenylamide having a melting point of 148° to 150°C were obtained.

2. 4-[3-methyl-benzofuranyl-(2)]-benzoic acid-o-amino-phenylamide 37.2 of 4-[3-methyl-benzofuranyl-(2)]-benzoic acid-o-nitro-phenylamide were dissolved in 370 ml of dimethylformamide. This solution was introduced into a stirring autoclave together with 4 g of Raney-Nickel and hydrogenated at room temperature while impressing 100 atmospheres of hydrogen. When hydrogenation was finished, the reaction mixture was rinsed with a small amount of dimethylformamide. The clear solution was then heated to 100°C and mixed dropwise, while stirring, with about 740 ml of water.

When the total amount of water was added, the mixture was allowed to slowly cool to room temperature. The product precipitated was suction-filtered, washed with water and dried.

This crude product was purified by recrystallization from toluene or chlorobenzene, while clearing with charcoal. 28.4 g (83 % of the theory) of 4-[3-methyl-benzofuranyl-(2)]-benzoic acid-o-amino-phenylamide having a melting point of 203° to 205°C were obtained.

3. 1-[3-methyl-benzofuranyl-(2)]-4-[benzimidazolyl-(2)]-benzene (Table 3, No. 302)

a. from 4-[3-methyl-benzofuranyl-(2)]-benzoic acid-o-aminophenylamide 34.2 g of 4-[3-methyl-benzofuranyl-(2)]-benzoic acid-o-aminophenylamide were introduced, while stirring, into 260 ml of o-dichlorobenzene. 0.3 g of o-toluene-sulfonic acid was added and the reaction mixture was heated while stirring, for 2 hours at about 175°C. The water formed in the reaction and a small amount of o-dichlorobenzene were distilled off via a descendant cooler.

Then the reaction mixture was filtered hot. After cooling to room temperature the crystallized product was suction-filtered, washed with o-dichlorobenzene and benzene and dried. This crude product was recrystallized from chlorobenzene while clarifying with charcoal. 21.4 g (66 % of the theory) of 1-[3-methyl-benzofuranyl-(2)]-4-benzimidazolyl-(2)]-benzene (Table 3, No. 302) having a melting point of 252° to 254°C were obtained.

b. from 4-[3-methyl-benzofuranyl-(2)]-benzoic acid-o-nitrophenylamide.

21.5 g of iron filings were introduced, while stirring, into a mixture of 750 ml of dimethylformamide and 125 ml of water.

4.5 ml of concentrated hydrochloric acid were added and the whole was heated to about 80°C. At this temperature 37.2 g of 4-[3-methyl-benzofuranyl-(2)]-benzoic acid-o-nitrophenylamide were introduced.

The reaction mixture was heated to the boil for 5 hours while stirring. After filtering the iron sludge the filtrate was mixed dropwise at about 100°C with 90 ml of a 4 N sodium carbonate solution, boiled up and filtered hot.

At 100°C, 525 ml of water were added to the clear solution so obtained. After cooling to room temperature the product precipitated was suction-filtered, washed with water and dried. This crude product was recrystallized for purification while clarifying with charcoal from chlorobenzene or toluene.

26.5 g (82 % of the theory) of 1-[3-methyl-benzofuranyl-(2)]-4-[benzimidazolyl-(2)]-benzene (Table 3, No. 302) having a melting point of 250° to 252°C were obtained.

In an analogous way were prepared the imidazolyl compounds listed in Table 3.

TABLE 3

| No. | A¹ | A² | A³ | X | B¹ | B² | B³ | melting point °C | absorption λmax nm | ε · 10⁻⁴ |
|---|---|---|---|---|---|---|---|---|---|---|
| 301 | H | H | H |  | H | H | H | 306–307 | 349 | 6,40 |
| 302 | H | H | CH₃ |  | H | H | H | 252–254 | 350 | 5,54 |
| 303 | CH₃ | CH₃ | H |  | H | H | H | 350–352 | 353 | 6,34 |
| 304 | H | OCH₃ | H |  | H | H | H | 282–284 | 357 | 6,21 |
| 305 | CH₃ | CH₃ | H |  | H | CH₃ | CH₃ | 362–364 | 359 | 6,72 |
| 306 | H | H | H | 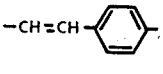 | H | H | H | 288–289 | 348 | 3,00 |
| 307 | H | H | H | —CH=CH—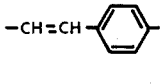 | H | H | H | 278–279 | 372 | 7,58 |
| 308 | H | H | H | —CH=CH— | CH₃ | H | H | 190–191 | 360 | 6,08 |
| 309 | H | H | H |  | H | CH₃ | H | 272–273 | 353 | 5,92 |
| 310 | H | H | H |  | H | CH₃ | CH₃ | 308–309 | 356 | 5,93 |
| 311 | H | H | H |  | CH₃ | CH₃ | H | 210–211 | 337 | 4,86 |
| 312 | H | H | H |  | CH₃ | H | CH₃ | 237–238 | 336 | 4,65 |
| 313 | H | H | H |  | CH₃ | CH₃ | CH₃ | 260–261 | 339 | 4,90 |

TABLE 3-continued

[Structure: benzofuran-X-benzimidazole with substituents A¹, A², A³ on benzofuran and B¹, B², B³ on benzimidazole]

| No. | A¹ | A² | A³ | X | B¹ | B² | B³ | melting point °C | absorption λmax nm | $\epsilon \cdot 10^{-4}$ |
|---|---|---|---|---|---|---|---|---|---|---|
| 314 | H | H | H | —CH=CH— | H | H | H | 258–260 | 360 | 5,52 |
| 315 | H | H | H | —CH=CH— | CH₃ | H | H | 144–146 | 369 | 4,73 |

EXAMPLE D:

Preparation of 1-[benzofuranyl-(2)]-4-[1,3-dimethyl-imidazolium-(2)]-benzene-methosulfate (Table 4, No. 401)

32.4 g of 1-[benzofuranyl-(2)]-4-[1-methyl-imidazolyl-(2)]-benzene were suspended in 400 ml of benzene and dissolved by heating to the boil. While stirring and boiling continuously 20 ml of dimethyl sulfate were added dropwise in the course of half an hour and the reaction mixture was heated further to the boil for about 5 hours.

Then the mixture was cooled to room temperature, the product precipicated was suction-filtered and washed with benzene. This crude product was purified by recrystallization from n-butyl alcohol, while clarifying with charcoal.

39.2 g (87 % of the theory) of 1-[benzofuranyl-(2)]-[1,3-dimethyl-imidazolium-(2)]-benzene-methosulfate (Table 4, No. 401) having a point of decomposition of 238° to 240°C were obtained.

In analogous way the other imidazolium compounds listed in Table 4 were obtained by quaternization of the corresponding N-substituted imidazols.

TABLE 4

[Structure: benzofuran with A¹, A², A³, A⁴ substituents linked via X to 1,3-dimethyl-benzimidazolium cation, with CH₃OSO₃⁻ counterion]

| No. | A¹ | A² | A³ | A⁴ | X | melting point (decomposition)°C | absorption λmax nm | $\epsilon \cdot 10^{-4}$ |
|---|---|---|---|---|---|---|---|---|
| 401 | H | H | H | H | —C₆H₄— | 238–240 | 330 | 3,76 |
| 402 | H | H | H | CH₃ | —C₆H₄— | 224–226 | 331 | 3,28 |
| 403 | H | CH₃ | CH₃ | H | —C₆H₄— | 252–254 | 341 | 3,66 |
| 404 | HC=CH–C=CH (fused ring) | | | H | —C₆H₄— | 212–213 | 360 | 3,78 |
| 405 | H | H | H | H | —CH=CH— | 202–210 | 363 | 3,29 |

EXAMPLE 1:

10 mg of the compound 201 (Table 2) were dissolved in 4 ml of dimethylformamide and dispersed by addition of a commercial nonionogenic dispersing agent in 100 ml of water at 60°C.

At this temperature 0.3 ml of formic acid was added and a 5 g polyacrylonitrile fabric was introduced into the bath thus obtained. The temperature was increased within 15 minutes to 95°–98°C, and the fabric was moved continuously at this temperature for 1 hour. The fabric was rinsed hot and cold and dried at the air.

The fabric thus treated showed a white brilliant appearance.

When proceding according to the above Example but using instead of the brightener mentioned the compounds 202 and 203 (Table 2) or 301 (Table 3) similar results were obtained.

EXAMPLE 2:

10 mg of the compound 201 (Table 2) were dissolved in 4 ml of dimethylformamide and, after addition of a non-ionogenic dispersing agent, dispersed in 100 ml of an aqueous solution which contained 100 mg of sodium chlorite. The liquid thus obtained was adjusted to pH 2 with 4N sulfuric acid and heated to 80°C. At this temperature a 5 g polyacrylonitrile fabric was added. It was bleached for 2 hours at 80°C, the bath heated in 20 minutes to 100°C and maintained at this temperature for about half an hour.

The fabric was rinsed with hot and cold water and dried at the air.

After drying the fabric showed an excellent degree of whiteness. This degree was determined with the ZEISS-ELREPHO apparatus according to the formula for the degree of whiteness according to Berger. The fabric treated as above had a degree of whiteness of 140 as compared with 83 of the material only pre-bleached.

Table 5 lists the degrees of whiteness obtained according to the above process with imidazolyl compounds.

TABLE 5

| Brightener | Degree of whiteness according to Berger | |
|---|---|---|
| | pH 2 | pH 3.5 |
| 201 | 140 | — |
| 202 | 135 | 108 |
| 203 | 123 | 113 |
| 301 | 142 | 109 |
| 302 | 140 | 134 |

The degree of whiteness of the material only pre-bleached was 72 at pH 3.5 and 83 at pH 2.

EXAMPLE 3:

10 mg of the compound 403 (Table 4) were dissolved in 100 ml of an aqueous solution which contained 0.2 g of sodium nitrate and 0.2 g of a 80 % sodium chlorite. By dropwise addition of 4N sulfuric acid the pH-value was adjusted to 2. The bath thus obtained was heated to 60°C and a 5 g polyacrylonitrile fabric was added. In 15 minutes the temperature was increased to 95°–98°C and the bath was maintained for 60 minutes at this temperature. The fabric thus treated showed a degree of whiteness of 123 as compared with 83 of the material only pre-bleached.

EXAMPLE 4:

A fabric of cotton was treated at a goods-to-liquor ratio of 1 : 20 with a bath which contained 5 g/l of a laundry softening agent having the following composition:

10 % of distearyl-dimethyl-ammonium chloride
2 % of butanediol-acetate-polyglycol ether (having, on an average, 8 ethylene-glycol units)
2 % of ammonium acetate
85.8 % of water
0.2 % of the compound 402 (Table 4)

The fabric was treated for 15 minutes at 25°C, rinsed and dried. After 1 and 10 treatments the cotton fabric showed the following degrees of whiteness (according to Berger).

| | degree of whiteness |
|---|---|
| untreated material | 83 |
| treated once | 112 |
| treated 10 times | 124 |

We claim:
1. A compound of the formula

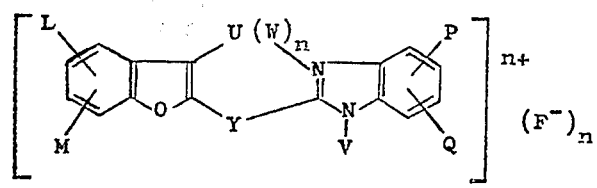

in which L, M, P and Q are hydrogen, halogen, lower alkyl, lower alkoxy or phenyl of L and M together or P and Q together are a cyclohexenyl or phenyl ring annellated at the positions 4 and 5; U is hydrogen, lower alkyl or phenyl; V is hydrogen, lower alkyl, benzyl, phenyl or phenyl substituted by chlorine, methyl or methoxy; W is lower alkyl, cyanomethyl, carbamylmethyl, carboxymethyl, lower carboalkoxymethyl, benzyl or benzyl substituted in the phenyl moiety by chlorine, methyl of methoxy; Y is a group of the formula

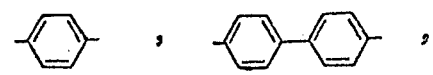

$n$ is zero or 1 and F is a colorless anion.

2. A compound of the formula

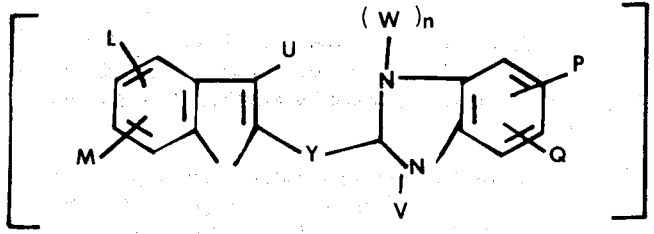

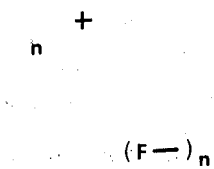

in which L, M, P and and Q are hydrogen, chlorine, lower alkyl or lower alkoxy or L and M together or P and Q together are a cyclopentenyl, cyclohexenyl or phenyl ring annellated at the positions 4 and 5; U is hydrogen or methyl; V is hydrogen or methyl; W is methyl or benzyl; Y is phenylene or naphthylene; n is zero or 1 and F is halogen, lower alkyl sulfate, lower alkysulfonate, phenylsulfonate or tosylate.

3. A compound as defined in claim 1, wherein L, M, P and Q are hydrogen, methyl or methoxy and L and M together and P and Q together are annellated phenyl at the positions 4 and 5; U is hydrogen or methyl; V is hydrogen or methyl; W is methyl; Y is a group of the formula

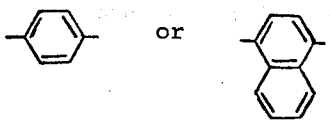

$n$ is zero or 1 and F is chloride or methosulfate.

4. The compound as claimed in claim 1, in which L, M, P, Q, U and V are hydrogen, Y is p-phenylene and $n$ is zero.

5. The compound as claimed in claim 1, in which L, M, P, Q, and U are hydrogen, V is methyl, Y is p-phenylene and $n$ is zero.

6. The compound as claimed in claim 1, in which L, M, P, Q and V are hydrogen, U is methyl, Y is p-phenylene and $n$ is zero.

7. The compound as claimed in claim 1, in which L, M, P and Q are hydrogen, U and V are methyl, Y is p-phenylene and $n$ is zero.

8. The compound as claimed in claim 1, in which P, Q and U are hydrogen, L is 5-methyl, M is 6-methyl, V is methyl, Y is p-phenylene and $n$ is zero.

9. The compound as claimed in claim 1, in which P, Q and U are hydrogen, L is 5-methyl, M is 6-methyl, V and W are methyl, Y is p-phenylene, $n$ is one and R is methosulfate.

10. The compound as claimed in claim 1, in which L, M, P and Q are hydrogen, U, V and W are methyl, Y is p-phenylene, $n$ is one and F is methosulfate.

* * * * *